(12) United States Patent
Piluiko

(10) Patent No.: US 12,076,066 B1
(45) Date of Patent: Sep. 3, 2024

(54) METHOD AND DEVICE FOR BONE FIXATION

(71) Applicant: Vitaly Piluiko, Las Cruces, NM (US)

(72) Inventor: Vitaly Piluiko, Las Cruces, NM (US)

( * ) Notice: Subject to any disclaimer, the term of this patent is extended or adjusted under 35 U.S.C. 154(b) by 0 days.

(21) Appl. No.: 17/676,126

(22) Filed: Feb. 19, 2022

Related U.S. Application Data

(60) Provisional application No. 63/151,791, filed on Feb. 21, 2021.

(51) Int. Cl.
  *A61B 17/88* (2006.01)
  *A61B 17/80* (2006.01)
  A61B 17/56 (2006.01)

(52) U.S. Cl.
  CPC ............. *A61B 17/88* (2013.01); *A61B 17/80* (2013.01); *A61B 17/808* (2013.01); *A61B 2017/564* (2013.01)

(58) Field of Classification Search
  CPC ... A61B 17/56; A61B 2017/564; A61B 17/80; A61B 17/8004; A61B 17/8019; A61B 17/808; A61B 17/88; A61B 17/8866; A61B 17/8872
  See application file for complete search history.

(56) References Cited

U.S. PATENT DOCUMENTS

| | | | |
|---|---|---|---|
| 5,951,557 A * | 9/1999 | Luter | A61B 17/80 606/71 |
| 8,167,891 B2 * | 5/2012 | Terres | A61B 17/8019 606/105 |
| 9,011,507 B2 * | 4/2015 | Schelling | A61B 17/8042 606/105 |
| 10,076,372 B2 * | 9/2018 | Madjarov | A61F 2/44 |
| 10,136,932 B2 * | 11/2018 | Freese | A61B 17/86 |
| 2010/0262193 A1 * | 10/2010 | Frigg | A61B 17/8019 606/281 |
| 2017/0181779 A1 * | 6/2017 | Leither | A61B 17/8057 |

* cited by examiner

*Primary Examiner* — Larry E Waggle, Jr.
(74) *Attorney, Agent, or Firm* — Fred Zollinger

(57) ABSTRACT

A method and device for repairing a bone fracture include the use of a bone plate and a bone hook that engages the interior of the bone. The method includes the steps of using at least one bone hook that engages the interior of the bone to apply a counterforce to the bone plate installation forces. The bone plate is configured to be positioned over the hook while the bone hook is in place. In an exemplary configuration, two bone hooks are used to position and then hold the ends of the fractured bone. The hooks are positioned through the bone plate and apply a counterforce to the installation of the bone plate. The hooks are removed after the plate is installed. In the case of a rib fracture, with the hook or hooks engaging the interior of the bone, there is minimal disruption to the intercostal material around the fracture and no engagement between the tools and the pleura behind the bone.

12 Claims, 8 Drawing Sheets

METHOD AND DEVICE FOR BONE FIXATION

CROSS REFERENCE TO RELATED APPLICATIONS

This application claims the benefit of U.S. Provisional Patent Application No. 63/151,791 filed Feb. 21, 2021; the disclosures of which are incorporated herein by reference.

BACKGROUND OF THE DISCLOSURE

1. Technical Field

The disclosure relates to bone plates and methods for installing bone plates. More particularly, the disclosure relates to the use of at least one bone hook that engages the interior of the bone to position and hold the bone while a bone plate is attached to the bone. Specifically, the disclosure provides an exemplary configuration wherein two bone hooks engage interior portions of the fractured bone to position the bone and then apply a counterforce during the installation of the bone screws. In this configuration, the bone hooks are positioned in a slot defined by the bone plate.

2. Background Information

Chest traumas, in particular rib fractures, are common. These fractures comprise about twelve percent of all fractures in patients, particularly the elderly. The most common complication of rib fractures is pneumonia which may be fatal. This is largely due to pain and splinting effects, preventing effective coughs and breathing. Treatment includes operative and non-operative methods. Pain medications and sometimes mechanical ventilation used in non-operative treatment may have major side effects. Non-operative treatment is associated with a prolonged stay in the hospital and possibly prolonged use of narcotic medications. Operative treatment is attractive as it may reduce long-term pain by immobilizing the broken edges of the bone and thus reducing pain. It involves alignment and stabilization of the rib fractures by using internal fixation devices or bone plates. Bone plates are stiff devices (usually metal such as titanium) positioned on the surface of the bone crossing the location of the fracture. The plate is connected to the bone with fasteners such as screws. A significant reduction in pneumonia rates has been found in surgically treated patients, 90% vs 22% at 21 days after surgery.

Although the use of bone plates is associated with desirable outcomes, the anatomy of the chest wall presents limitations to the use of the bone plates for several reasons. First, the underlying fine lining of the pleura can be easily violated with instrumentation leading to pneumothorax, potentially a life threatening condition. Second, between the ribs there is an intercostal space where the intercostal artery and nerve are found. Injury to these structures can occur leading to bleeding and excessive pain. Third, ribs are very soft bone and can bow away from the tools under the pressure of the drilling and screwing during the installation of the bone plate. Also, the procedure commonly requires holding the rib and plate with clamps. When clamps are used that engage the sides of the ribs, the intercostal material is violated. In order to apply these clamps, the incision of the chest wall has to be extended. Exposure of the rib/rib fractures may lead to a large incision which is an additional source of pain due to the incision size. Therefore, a minimally invasive incision that allows reliable reduction of the rib fracture and subsequent firm immobilization of the edges of the rib preventing even minimal movement may be ideal treatment of these injuries.

SUMMARY OF THE DISCLOSURE

The disclosure provides a method, a device, and a kit used to practice the method. The method includes the steps of using at least one bone hook that engages the interior of the bone to apply a counterforce to the bone plate installation forces. The bone plate is configured to be positioned while the bone hook is in place. In an exemplary configuration, two bone hooks are used to position and then hold the ends of the fractured bone. The bone plate is positioned about the bone hooks and positioned over the bone ends. The bone hooks are used to apply a counterforce that is in opposition to the forces required to install the fasteners that secure the bone plate to the bone. The bone hooks are removed after the bone plate is installed. In the case of a rib fracture, with the hook or hooks engaging the interior of the bone, there is minimal damage to the intercostal material around the fracture and no engagement between the tools and the pleura behind the bone. With the bone hooks passing through the center of the bone plate, the size of the incision is minimized.

In one configuration, the disclosure provides a bone plate that has a body that can be flat or curved to match the curvature of the bone on which it is to be used. The body has a central portion located between a first end portion and a second end portion. Each of the end portions defines at least one fastener hole. The central portion defines an elongated slot. The slot has a width and a length. In combination with the bone plate, first and second bone hooks are provided to define a bone plate installation kit. Each bone hook has a shank and a hook. In use, the shanks of the bone hooks are located in the slot of the bone plate. Each shank has a maximum cross sectional dimension (such as a diameter or a width) that is smaller than the width of the slot which allows the user to manipulate the bone hooks when they are through the plate.

In another configuration, the disclosure provides a bone plate that has a body that can be flat or curved to match the curvature of the bone on which it is to be used. The body has a central portion located between a first end portion and a second end portion. Each of the end portions defines at least one fastener hole. The central portion defines an elongated slot that is open to an edge of the body at a neck. The slot has a width and a length. The neck has a minimum width. In combination with the bone plate, first and second bone hooks are provided to define a bone plate installation kit. Each bone hook has a shank and a hook. In use, the shanks of the bone hooks are located in the slot of the bone plate. Each shank has a maximum cross sectional dimension (such as a diameter or a width) that is smaller than the width of the slot and smaller than the minimum width of the neck. This allows the bone plate to be moved onto the bone hooks by passing the bone hook shanks through the neck.

The individual features may be combined in different combinations than specifically described below to form different configurations of the device of the disclosure. The preceding non-limiting aspects of the disclosure, as well as others, are more particularly described below. A more complete understanding of the devices, assemblies, and methods can be obtained by reference to the accompanying drawings, which are not intended to indicate relative size and dimensions of the assemblies. In those drawings and the description below, like numeric designations refer to components of like function. Specific terms used in that description are intended to refer only to the particular structure of the embodiments selected for illustration in the drawings, and are not intended to define or limit the scope of the disclosure.

DETAILED DESCRIPTION OF THE DISCLOSURE

Figure 1:
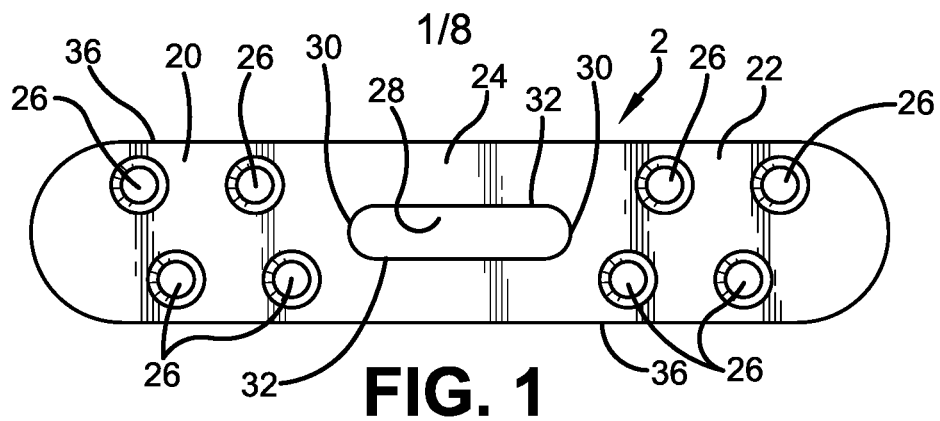
FIG. 1 is a top plan view of a first exemplary embodiment of the bone plate of the disclosure.

The disclosure provides a method, a device in the form of a bone plate 2, and a kit 4 used to practice the method. Kit 4 includes the combination of bone plate 2 and first and second bone hooks 6 that cooperate with bone plate 2. The method includes the steps of using at least one bone hook 6 to engage the interior of a fractured bone 10 to apply a counterforce to the bone plate installation forces. The bone hook 6 passes through the bone plate 2. In general, the method minimizes the size the incision required to operate on a bone fracture and the disruption to the material around the fracture is minimized. In the case of a rib fracture, with hooks 6 engaging the interior of bone 10, there is minimal damage to the intercostal material 12 around the fracture and no engagement between the tools and the pleura 14 behind bone 10.

Figure 2:
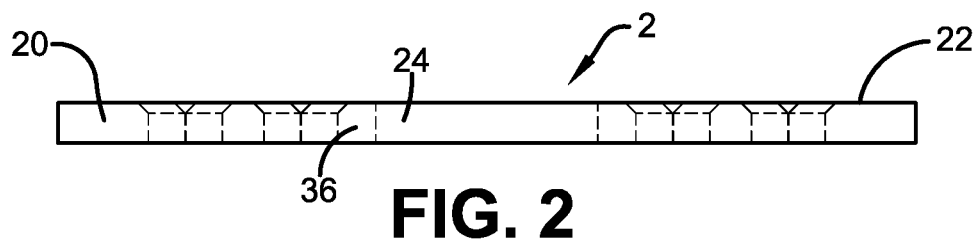
FIG. 2 is a front view of FIG. 1.
Figure 3:
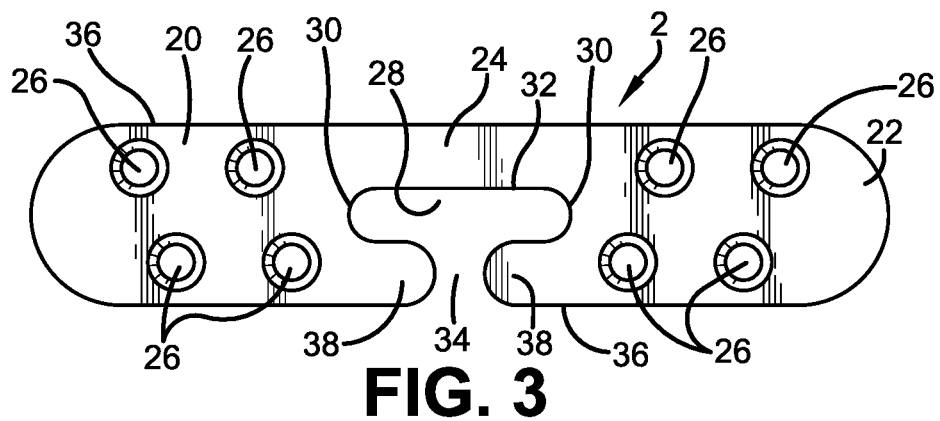
FIG. 3 is a top plan view of a second exemplary embodiment of the bone plate of the disclosure.
Figure 4:
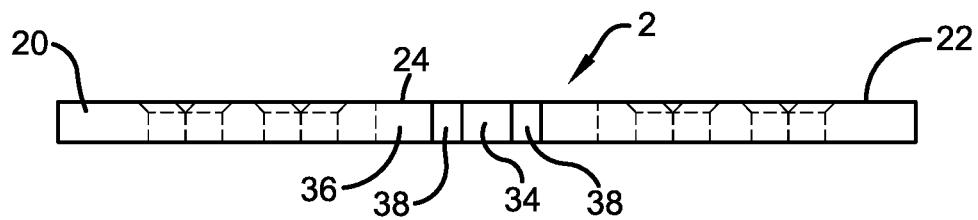
FIG. 4 is a front view of FIG. 3.
Figure 5:
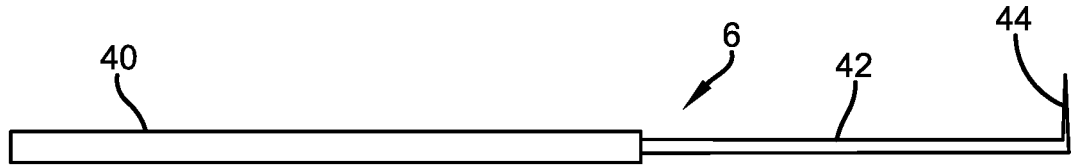
FIG. 5 is a side view of a bone hook that is used with the bone plate of the disclosure.
Figure 6:
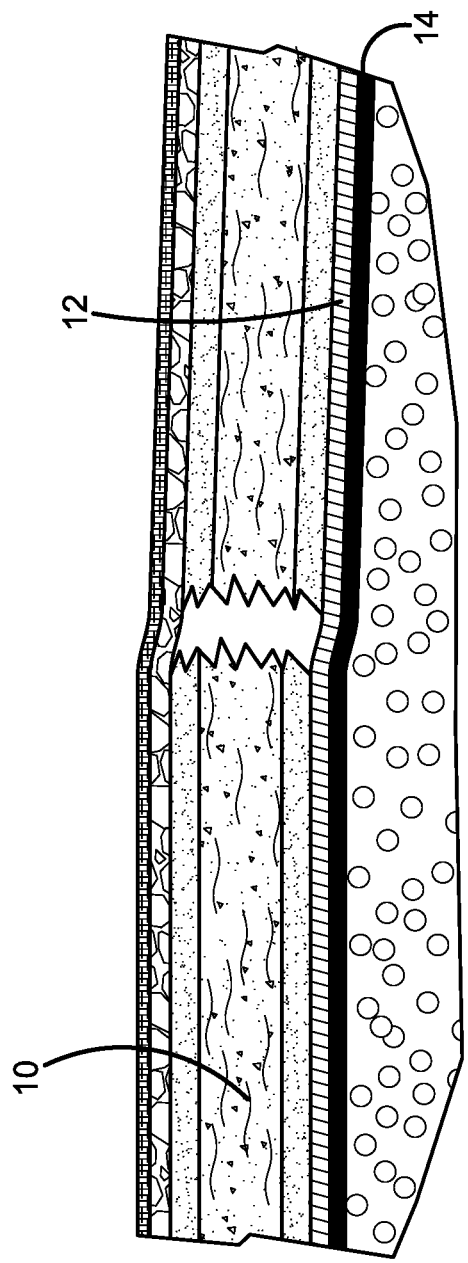
FIG. 6 is a section view of an exemplary bone fracture.
Figure 7:
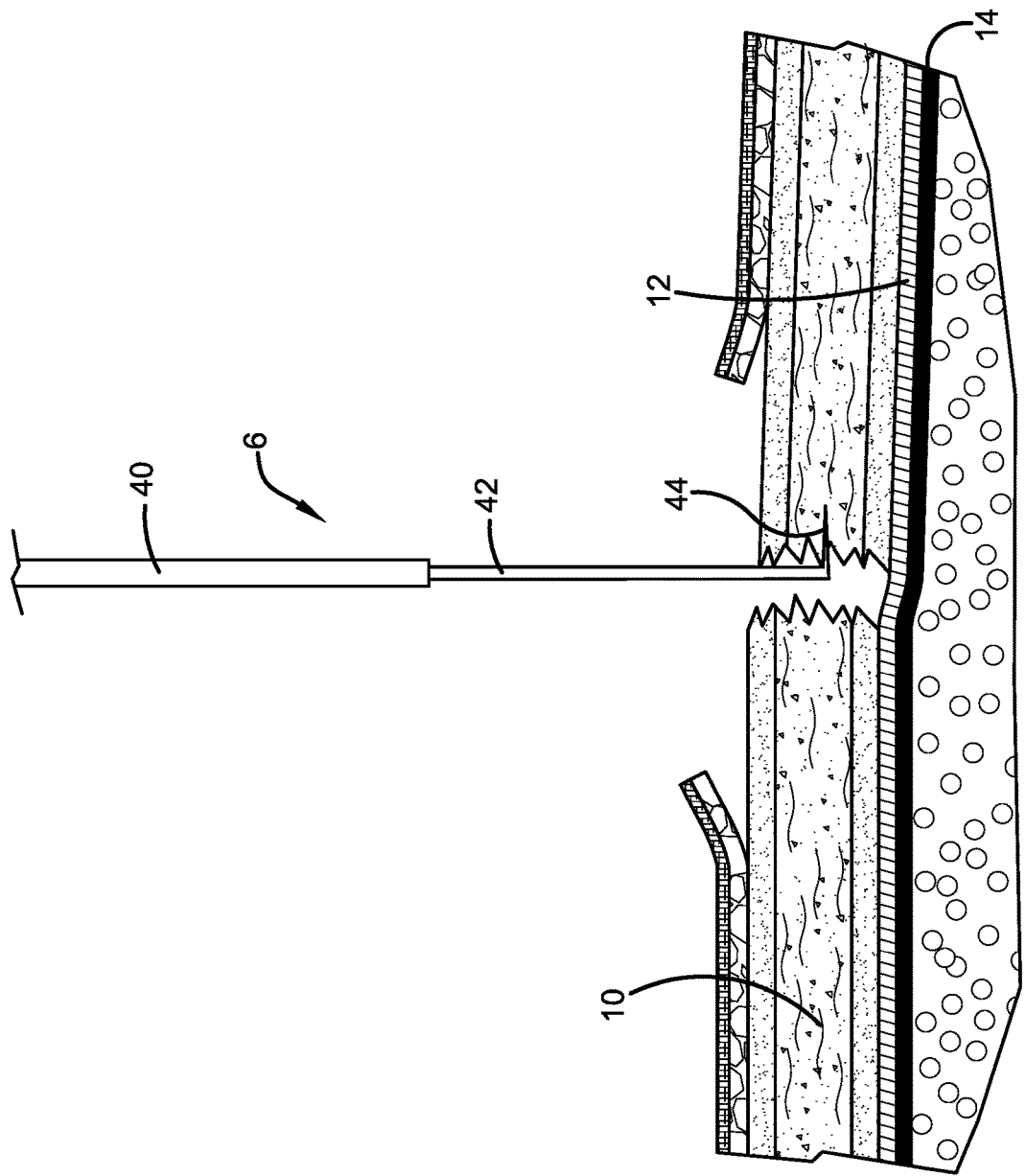
FIG. 7 is a view similar to FIG. 6 with a first bone hook inserted into a first bone end.
Figure 8:
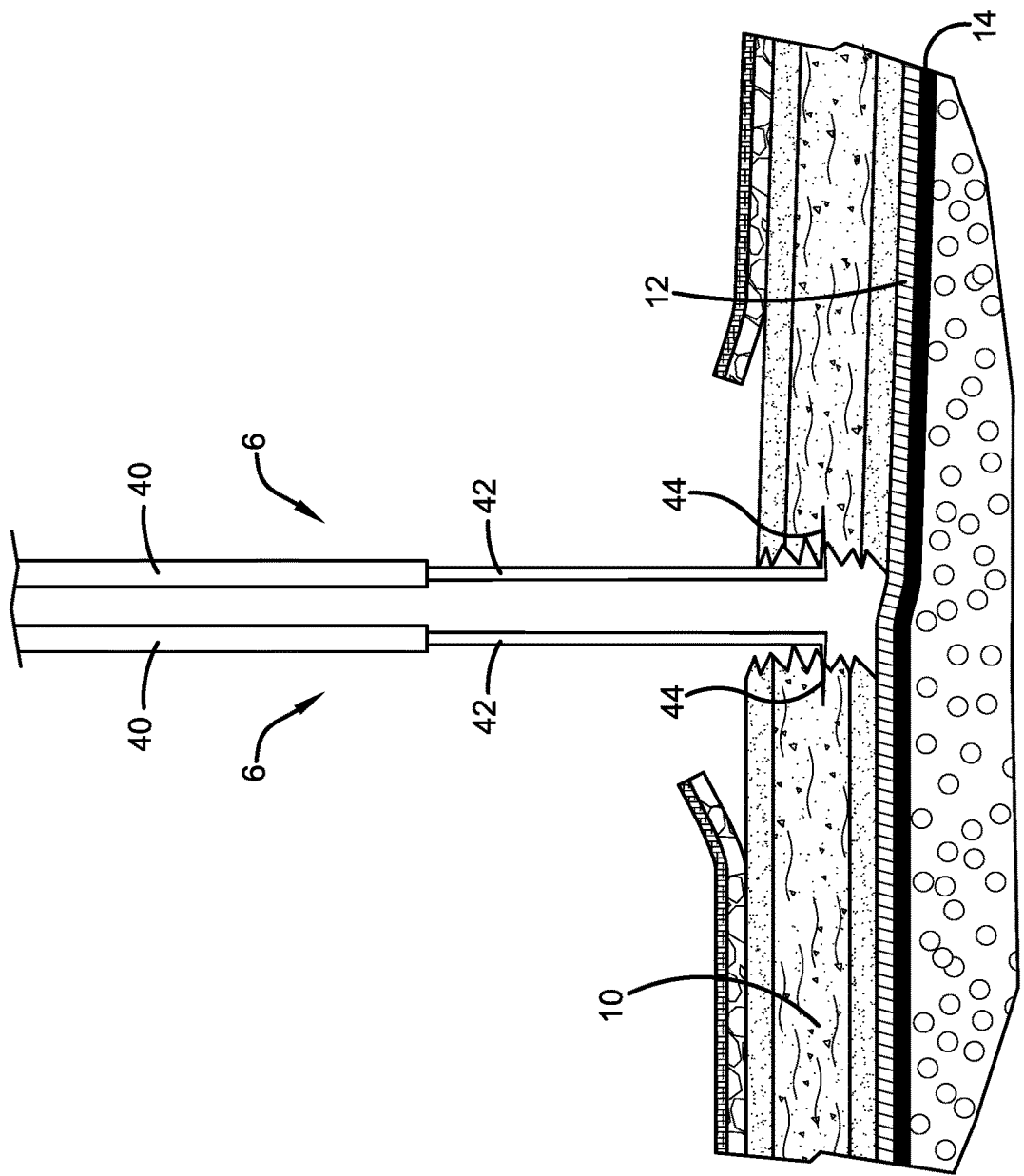
FIG. 8 is a view similar to FIG. 6 with a second bone hook inserted into a second bone end.
Figure 9:
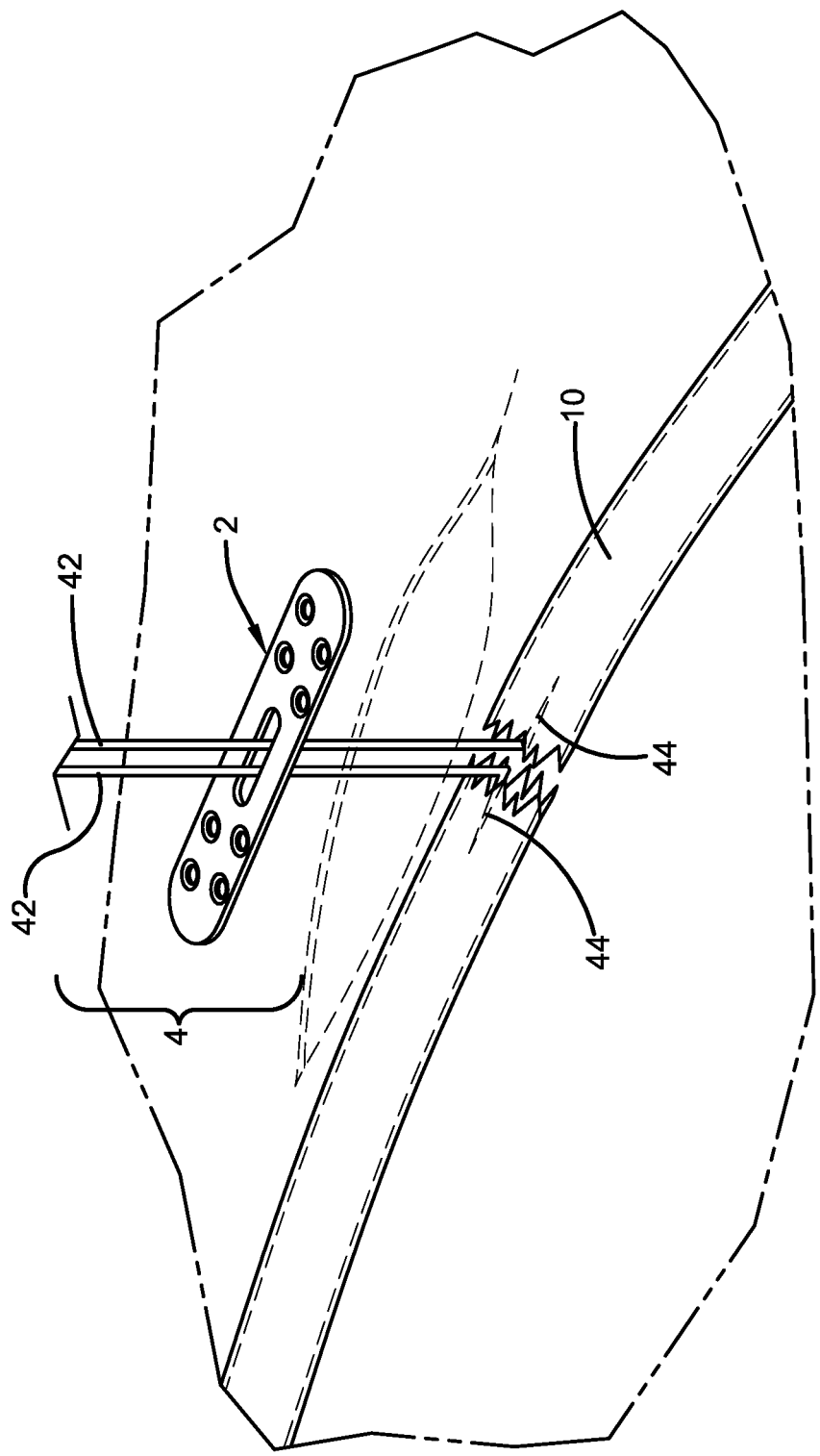
FIG. 9 is a perspective view showing how the bone ends have been repositioned with the bone hooks and a bone plate positioned over the bone hooks.
Figure 10:
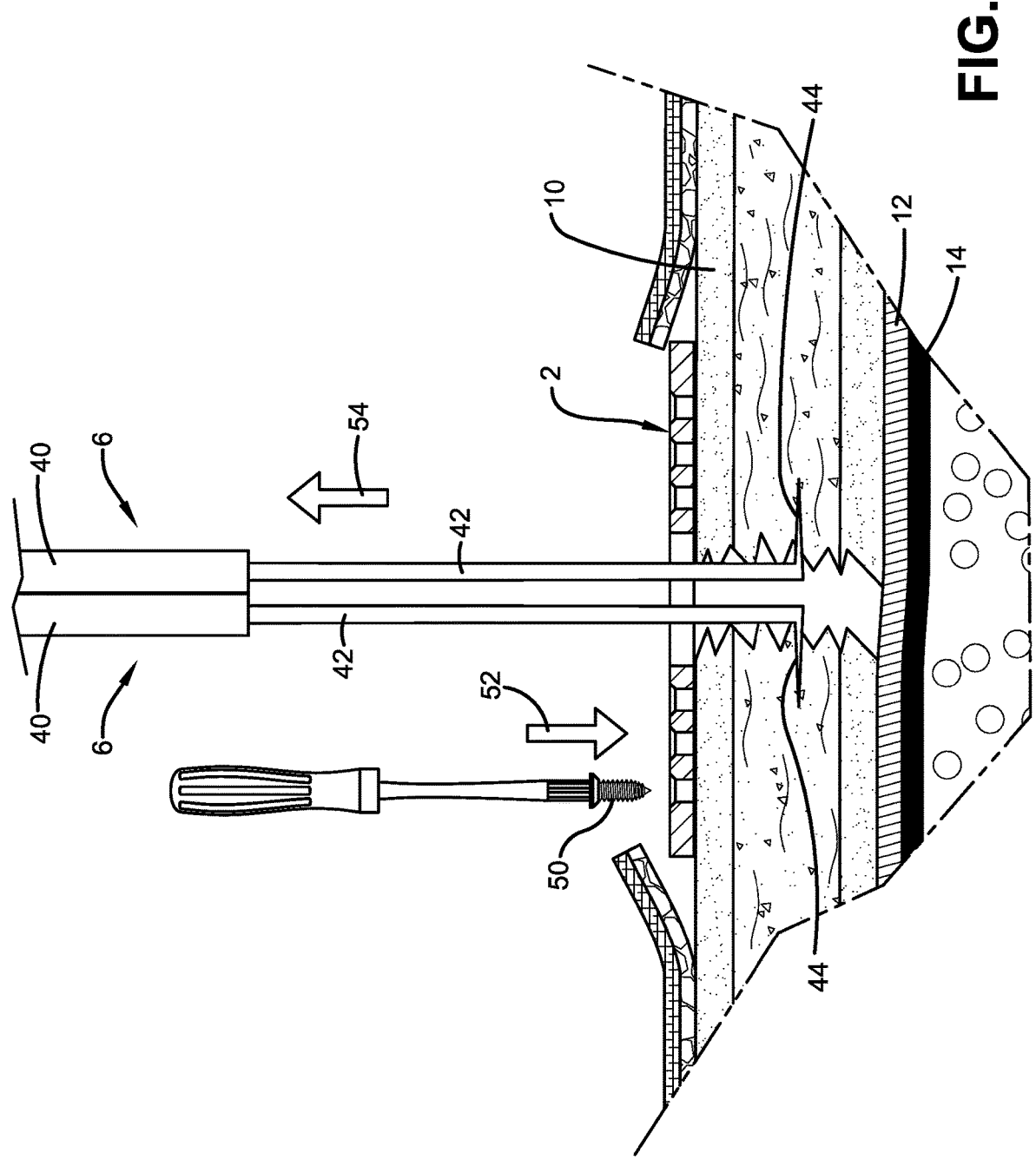
FIG. 10 is a view similar to FIG. 6 showing a counterforce being applied by the bone hooks while a first bone screw is installed.
Figure 11:
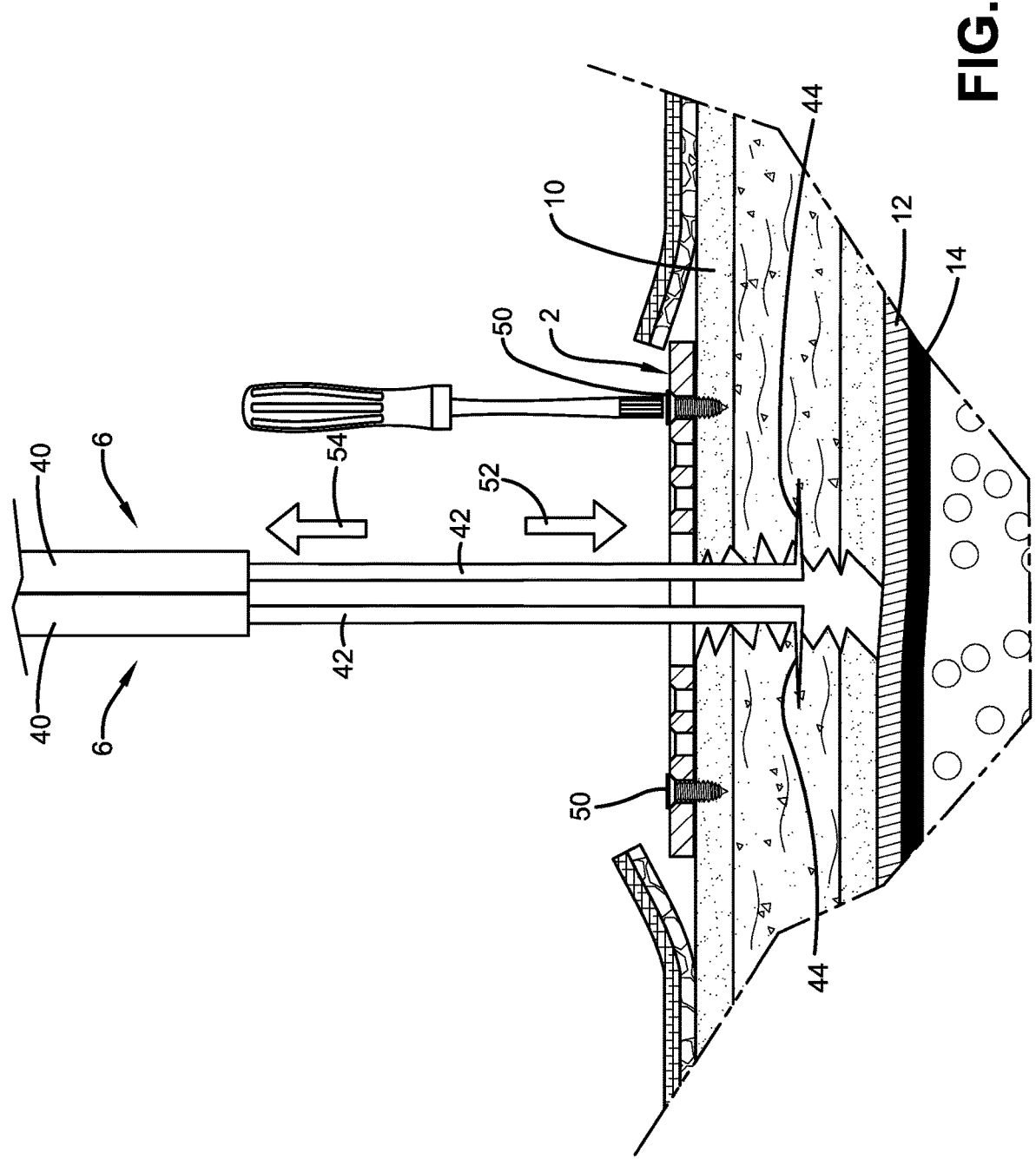
FIG. 11 is a view similar to FIG. 6 showing a counterforce being applied by the bone hooks while a second bone screw is installed.
Figure 12:
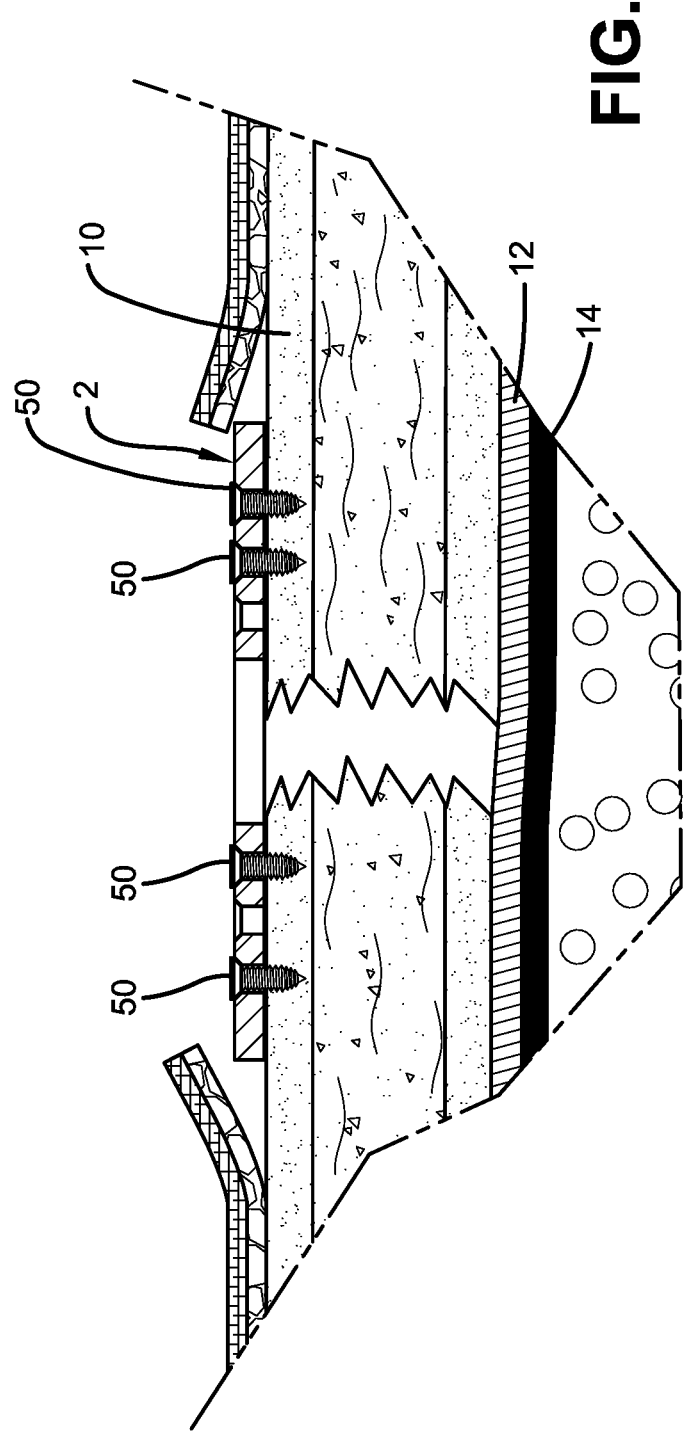
FIG. 12 is a view similar to FIG. 6 showing the bone plate installed and the bone hooks removed.

A first exemplary configuration of bone plate 2 is depicted in FIGS. 1 and 2. Although the exemplary configuration is depicted as being a flat plate, bone plate 2 can be curved about one or more of its axes to complement the shape of bone 10 with which it will be used. Bone plate 2 can be made from a biocompatible material such as stainless steel, cobalt base alloys, bioceramics, titanium alloys, pure titanium, composite materials, and polymers. Although the size and shape of the body of bone plate 2 varies for use with different bones, each body includes a first end portion 20, a second end portion 22, and a central portion 24. Each end portion 20 and 22 defines at least one fastener opening 26 that is configured to receive a fastener, such as a bone screw, that secures bone plate 2 to bone 10. In the exemplary configuration, fastener openings 26 are round openings. Each end portion 20 and 22 defines four fastener openings 26. In each end portion 20 and 22, fastener openings 26 are spaced from their edges the same distances such that two sets of two fastener openings 26 are aligned in the longitudinal direction of bone plate 2 in each end portion 20 and 22. Fastener openings 26 are offset from each other across the centerline of bone plate 2. Central portion 24 defines a slot 28 that is sized to loosely accommodate both bone hooks 6 at the same time. Slot 28 is elongated in the longitudinal direction of bone plate and can be centered with respect to the length and width of the body of bone plate 2. The ends 30 of slot are semi-circular. The walls 32 that define the sides of slot 28 are straight. Slot 28 has a width between walls 32 and a length between ends 30. In the exemplary configurations, the length is four times the width but in other configurations, the length of slot 28 can be two to eight times the width. In the second exemplary configuration, the body of bone plate 2 defines an open neck 34 that connects slot 28 with an edge 36. Neck 34 has a minimum opening between the two shoulders 38 that define neck 34. The ends of shoulders 38 are rounded. The minimum opening dimension can be the same as the width of slot 28 or slightly larger than the maximum dimension of the portion of bone hook 6 that is moved through neck 34 during the method.

Each bone hook 6 includes a handle 40, a shank 42, and a hook end 44. Handle 40 is optional. Shank 42 is a thin compared with the width of slot 28 and has a length sufficient to allow the user to place hook end 44 into fractured bone 10. Hook end 44 is tapered to a sharp point. Handle 40 and shank 42 are sized to fit through slot 28. The maximum lateral cross sectional dimension (such as a width or diameter) of handle 40 and shank 42 is smaller than the width of slot 28. Shank 42 is sized such that two shanks 42 can be located in slot 28 at the same time and moved around within slot 28. Bone plate 2 can thus be moved down over handle 40 and shank 42 or bone plate 2 can be moved onto shank 42 by passing shank 42 through neck 34. In the exemplary configuration, the maximum cross section shank dimension is about a third of the width of slot 28. In other configurations, the shank dimension is a tenth to two-thirds of the width of slot 28.

After surgical access and limited bone 10 exposure, hook ends 44 are placed in the bone marrow of both ends of the broken bone 10. The surgeon reduces the fracture by moving both ends of the broken bone 10 in opposing and aligned positions. As an option, temporary holding screws are drilled closely to the broken ends of the bone 10. As an option, hooks 6 and screws can be placed prior to the application of the hooks through the plate slot 28 first. With the ends of the bone 10 aligned, bone plate 2 is placed over bone hooks 6 with bone hooks 6 located in slot 28. In the second configuration, bone plate 2 is moved onto shanks 42 by passing shanks 42 through neck 34. Bone plate 2 is lowered over the bone 10. Bone plate 2 can be held in position with shanks 42. Using the bone hooks 6 (and optionally temporary screws) for holding the bone 10 in the aligned position, fasteners 50 such as fixating screws are placed through openings 26 into bone 10. The force 52 necessary for installing fasteners 50 down or inwardly is countered by the opposing force 54 holding bone hooks 6 (or optionally holding temporary screws) as they are pulled up. After fasteners 50 are installed, bone hooks 6 are removed.

The following are advantages of this method and use of this plate for rib fracture reduction and fixation:
 1. It accomplishes bone fixation with a minimal incision that only provides access to the area of the fracture.
 2. It allows visual realignment of the fractured segments of the rib 10 utilizing bone hooks 6.

3. It provides a counterforce 54 for application of the screws 50.
4. It provides an elongated slot 28 for placing the bone hooks 6.
5. The neck opening 34 in the bone plate 2 provides access to slot 28 for ease of applying the bone plate 2 around the bone hooks 6.
6. There is elimination of the need for applying clamps on the bone 10 and the bone plate 2 to affix them for drilling the screws 50.
7. It avoids opening the intercostal space and the pleural space with less trauma to the soft tissue.
8. The bone plate 2 is applied with the help of the bone hooks 6 or in combination with the bone hooks 6 and the holding drill for temporary bone suspension and as counterbalance for drilling the screws 50 into the bone 10.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the above description and attached illustrations are an example and the invention is not limited to the exact details shown or described. Throughout the description and claims of this specification the words "comprise" and "include" as well as variations of those words, such as "comprises," "includes," "comprising," and "including" are not intended to exclude additives, components, integers, or steps.

The invention claimed is:

1. A method of installing a bone plate over a fracture of a fractured bone; the method comprising the steps of:
   supporting one bone end on one side of the fracture with a first bone hook engaging an interior of the bone through the fracture;
   supporting the other bone end on the other side of the fracture with a second bone hook engaging the interior of the bone through the fracture;
   positioning the bone plate around portions of the first and second bone hooks by moving the first and second bone hooks through a slot defined by the bone plate such that both bone hooks are located in the same slot;
   positioning the bone plate over the fracture;
   supplying an outward force with at least one of the first and second bone hooks, the outward force opposing an inward force of installing fasteners that secure the bone plate to the bone; and
   removing the first and second bone hooks after the bone plate is secured to the bone.

2. The method of claim 1, further comprising the step of adjusting positions of the bone ends with the bone hooks before the step of positioning the bone plate around portions of the first and second bone hooks.

3. A method of installing a bone plate over a fracture of a fractured bone; the method comprising the steps of:
   supporting one bone end on one side of the fracture with a first bone hook engaging an interior of the bone;
   supporting the other bone end on the other side of the fracture with a second bone hook engaging the interior of the bone;
   positioning the bone plate around portions of the first and second bone hooks;
   positioning the bone plate over the fracture;
   supplying an outward force with at least one of the first and second bone hooks, the outward force opposing an inward force of installing fasteners that secure the bone plate to the bone;
   removing the first and second bone hooks after the bone plate is secured to the bone; and
   wherein the step of positioning the bone plate around portions of the first and second bone hooks includes the step of moving the bone hooks through an open neck and into a slot defined by the bone plate.

4. The method of claim 3, further comprising the steps of passing a portion of the first bone hook through a fractured end of the one bone end and passing a portion of the second bone hook through a fractured end of the other bone end.

5. The method of claim 4, further comprising the step of adjusting positions of the bone ends with the first and second bone hooks.

6. The method of claim 5, wherein the step of adjusting the positions of the bone ends is performed before the bone plate is positioned around portions of the first and second bone hooks.

7. The method of claim 3, wherein the step of positioning the bone plate around portions of the first and second bone hooks includes the step of moving both of the first and second bone hooks into the slot defined by the bone plate such that both the first and second bone hooks are in the same slot.

8. A bone plate installation kit comprising:
   a bone plate and first and second bone hooks;
   the bone plate having a central portion located between a first end portion and a second end portion;
   each of the end portions defining at least one fastener opening;
   the central portion defining an elongated slot having a length between slot ends and a minimum width;
   each bone hook having a shank and a hook end; the shank of each bone hook being sized to allow both shanks to be located in and move around in the elongated slot at the same time;
   each shank having a maximum width dimension that is no greater than two-thirds of the minimum width of the elongated slot; and
   wherein the bone plate has first and second edges; the elongated slot being open to one of the edges through a neck; the neck having an opening width sized greater than the maximum width dimension of each bone hook shank.

9. The kit of claim 8, wherein the elongated slot has a length that is at least two times and at most eight times the minimum width of the elongated slot.

10. A method of installing a bone plate over a bone fracture comprising the steps of:
    positioning a first bone hook through a slot in a bone plate;
    supporting one bone end on one side of the fracture of a fractured bone with the first bone hook by engaging an interior of the one bone end of the fractured bone through a fractured end of the fractured bone to provide an outward counterforce to an inward force of installing a bone fastener through the bone plate;
    positioning a second bone hook through the slot of the bone plate; and
    supporting the other bone end on the other side of the fracture of the fractured bone with the second bone hook by engaging an interior of the other bone end of the fractured bone through a fractured end of the fractured bone to provide an outward counterforce to an inward force of installing a bone fastener through the bone plate.

11. The method of claim 10, wherein the first and second bone hooks are positioned in the slot of the bone plate after the first and second bone hooks engage the bone interiors.

12. The method of claim 10, wherein the first bone hook is positioned in the slot of the bone plate after the first bone hook engages the bone interior.

\* \* \* \* \*